United States Patent [19]

Seifert et al.

[11] Patent Number: 5,096,824

[45] Date of Patent: Mar. 17, 1992

[54] SAPSTAIN CONTROL METHOD USING MARIANNAEA ELEGANS

[75] Inventors: Keith Seifert, Nepean; Colette Breuil, Vanier; Mary Mes-Hartree, North Gower, all of Canada

[73] Assignee: Forintek Canada Corp., Ottawa, Canada

[21] Appl. No.: 395,497

[22] Filed: Aug. 17, 1989

[51] Int. Cl.$^5$ .......................... C12N 1/20; A01N 63/00
[52] U.S. Cl. .................... 435/254; 435/267; 435/277; 424/93
[58] Field of Search ............ 435/254, 267, 277; 424/93

[56] References Cited

U.S. PATENT DOCUMENTS

| | | | |
|---|---|---|---|
| 3,255,095 | 7/1966 | Ricard | 435/254 |
| 3,424,655 | 1/1969 | Ricard | 435/254 |
| 3,993,752 | 11/1976 | Stutz | 424/658 |
| 4,400,298 | 8/1983 | Boocock et al. | 428/660 |
| 4,612,328 | 9/1986 | Jakubowski | 524/206 |

FOREIGN PATENT DOCUMENTS

| | | | |
|---|---|---|---|
| 963387 | 2/1975 | Canada | 435/254 |
| 1274291 | 5/1972 | United Kingdom | |
| 1573850 | 8/1980 | United Kingdom | 435/254 |

OTHER PUBLICATIONS

Seifert et al., Biological Abstracts, vol. 87(4), Feb. 15, 1989, #41574.
The ATCC Catalogue of Fungi and Yeasts, 17th Ed. 1987.
Seifert et al., "Screening for Microorganisms with the Potential for Organism" 23.13d. 1988 Heft 2.
Seifert, "Biological Control and Wood Protection" Canadian Wood.
Unligil, H. H. 1978, Decay Resistance of Wood Treated with Fungal Antibiotics: Cryptosporiopsin, Hyalodendrin, and Scytalidin. Wood. Sci. 11: 30–32.
Shields, J. K. 1966. Wood Pathology. Rept. For. Prod. Res. Branch, Dept. For. Can., Apr. 1964–Mar. 1965: 48–52.
Shields, J. K. 1968. Role of Trichoderma viride in Reducing Storage Decay of Birch Logs. Bimonthly Res. Notes Dept. For. Can. 24: 9–10.
Hulme, M. A. et al. 1972. Effect of Primary Fungal Infection Upon Secondary Colonization of Birch Bolts. Mat. und Org. 7: 177–188.
Stilwell, M. A. 1966. A growth Inhibitor Producted by Cryptosporiopsis sp., An Imperfect Fungas Isolated from Yellow Birch, Betula alleghaniensis Britt. Can. J. Bot. 44: 249–267.
Strunz, G. M., et al., Structure of Cryptosporiopsin: A New Antibiotic Substance Produced by a Species of Cryptosporiopsis. Can. J. Chem. 47: 2087–2094.
Bergman, O. et al., 1979. Outdoor Chip Storage Methods of Reducing Deterioration During OCS. pp. 245–271. In: Chip Quality Monograph. Edited by J. V. Hatton. Pulp and Paper Tech. Ser. No. 5.
Stilwell M. A. et al., 1967. Antibiotic Produced by a Fungus. Rept. CFS For. Res. Lab., Fredericton, N. B.
Stilwell, M. A. et al., 1973. Production, Isolation and Antifungal Activity of Scytalidin, A Metabolites of Scytalidium sp. Can. J. Micro-biol. 19: 597–602.
Strunz, G. M. et al., 1973. Scytalidin: A New Fungitoxic Metabolite Produced by a Scytalidium Species. J. Chem. Soc. Perkin Trans. 1: 2280–2283.
Stranks, D. 1976. Scytalidin, Hyalodendrin, Crypto-Sporiopsis—Antibiotics for Prevention of Blue Stain in White Pine Sapwood. Wood. Sci. 9: 110–112.
Seifert, K. A. et al., Screening of Microorganisms with the Potential for Biological Control of Sapstain on Unseasoned Lumber. Mat. und Org.: 23 BD Heft 2.
Bernier, R. et al., 1986. Antagonistic Effect Between Bacillus subtilus and Wood Staining Fungi. J. Inst. Wood. Sci. 10: 214–216.
Benko, R. 1988. Acteria as Possible Organisms for Biological Control of Blue Stain. Int. Res. Group on Wood Preserv., Document No. IRG/WP/1339.
Johnson, B. R. 1986. Sensitivity of Some Wood Stain and Mold Fungi to an Inhibitor of Chitin Synthesis. For. Prod. J. 36(3): 54–56.
Benko, R. 1987, Antagonistic Effect of Some Mycorrhizal Fungi as Biological Control of Sapstain. Int. Res. Group on Wood Preserv., Document No. IRG/WP/1814.

Primary Examiner—Ronald W. Griffin
Assistant Examiner—Pamela S. Webber
Attorney, Agent, or Firm—Iver P. Cooper

[57] ABSTRACT

The invention relates to a method for controlling or preventing sapstain in wood or wood products using the fungus Mariannaea elegans as a biological control agent. The method comprises treating the wood or wood products with an inoculum of Mariannaea elegans.

16 Claims, No Drawings

SAPSTAIN CONTROL METHOD USING MARIANNAEA ELEGANS

The present invention consists of a method of protecting lumber, especially unseasoned softwood lumber, against unwanted sapstain by inoculation of said lumber with the unique biological control microorganism, *Mariannaea elegans* (Fungi: Hyphomycetes), that either prevents the growth of undesirable sapstaining organisms, or prevents the formation of discolourations by these organisms.

The biological control organism is a fungus that does not itself decay or discolour the wood to any objectionable extent, and comprises one or more of the following strains: *Mariannaea elegans* FTK 386A, 386B, 386C, 386D, 386E, 386F or 386G.

Sapstain of unseasoned lumber is a cosmetic defect that is considered objectionable by many buyers. These discolorations, caused by a variety of microfungi, are a serious problem on lumber stored in lumber yards after sawing, but prior to planing and chemical treatment, and also on untreated lumber that is exported abroad. For the Canadian forest products industry, hem-fir products, spruce-pine-fir or white pine products are particularly prone to sapstain.

Several phenomena combine to create the discolorations. Sapstaining fungi generally discolour the wood brown, grey or black. The stain is caused by the pigmented fungal hyphae that accumulate in the cells of the sapwood, particularly in the rays. There is also evidence that dense accumulations of unpigmented hyphae in the wood tissue can cause similar discolorations. Some microfungi discolour wood by the production of coloured spores or sporulating structures. In addition, some species discolour wood red, purple, green or yellow by producing extracellular pigments that diffuse into the wood tissues.

Sapstainers are primary colonizers of wood that subsist mainly on soluble nutrients. Although they cause little structural damage, they are perceived as forerunners of decay fungi by many consumers, and thus the objection to sapstain discoloration may have a more practical basis than just aesthetics.

Many different chemicals have been used to control sapstain. In Canada, the most widely used chemicals have been the chlorinated phenols, particularly sodium penta- and tetrachlorophenol (PCP). PCP, although effective against most sapstain and mould fungi, is highly toxic to mammals and fish and persists in the environment. Furthermore, PCP contains toxic impurities such as dioxin that make its continued use a cause for public concern. Other chemical protection agents are being studied around the world to replace PCP. In Canada, formulations incorporating the chemicals TCMTB, copper-8-quinolinolate or borax are receiving serious attention.

Biological control is a relatively new concept in forest products. In biological control, a "harmless organism", in this case one that does not decay or discolour wood, is deliberately added to a product in order to prevent, retard or stop the growth of undesirable organisms. The most widely used biological control agent is the bacterium *Bacillus thuringiensis*, better known as BT, which is used to control spruce budworm in Ontario and parts of Quebec. The bacterium produces a toxic crystal that is eaten by the budworm as it eats the leaves, eventually killing the pest. Approximately half a dozen biological control systems have been marketed for agricultural use, for example DeVine, a fungal control of parasitic vines in citrus orchards. Below, some examples of biological control related to wood products pathology are reviewed.

The best known example of biological control in forest products relates to the control of decay in wooden transmission poles by the injection into the wood tissue of a dart containing spores or mycelium of "immunising commensals", as described by J. Ricard in Canadian patents Nos. 963,387 and 1,106,201. Ricard claims a wide range of applications for his invention, but these relate to inoculating biological control agents into wood tissue and further does not teach the prevention of sapstain in wood or wood products.

Several research teams around the world have published results of screening programs for biological control organisms for the prevention of wood decay. The concept of Ricard, using mixtures of Trichoderma spp. and Scytalidium sp. to control decay in transmission poles, has been investigated by other research teams in the United Kingdom, the United states and the Federal Republic of Germany. Antifungal metabolites of Scytalidium sp. have been isolated and chemically characterised, along with antifungal metabolites from Hyalodendron sp. and Cryptosporiopsis sp., and these metabolites have been applied to wood in an attempt to prevent decay.[1]

A second possible application of biological control organisms is round wood in storage. Shields[2] reported that decay by *Bjerkandera adusta, Coriolus hirsutus* and *C. versicolor* was inhibited in wood blocks precolonized with *Trichoderma harzianum* or an unidentified strain (now known to be *Scytalidium lignicola*). The strain of *T. harzianum* was later used in a field test on birch bolts[3] where a conidial suspension was sprayed onto freshly cut ends of birch bolts. After a two week precolonization period, *Bjerkandera adusta* was inoculated onto the bolts. After six months, very little *B. adusta* was reisolated from the bolts.

Stilwell[4] isolated a strain of Cryptosporiopsis sp. from yellow birch that inhibited the growth of 31 decay fungi in agar interactions. Decay of blocks by *Fomes fomentarius* was inhibited in precolonization experiments. In a field test, decay was reduced in peeled birch logs inoculated with a water suspension of Cryptosporiopsis sp., but no significant difference was noted in unpeeled logs. Culture filtrates of Cryptosporiopsis also inhibited growth of *F. fomentarius*. The antibiotic metabolite was purified, characterized and given the name cryptosporiopsin[5].

Decay of wood chips during storage was also considered as a possible target for antagonistic microorganisms. Bergman and Nilsson[6] tested several mould fungi isolated from wood chips for their ability to inhibit chip decay in laboratory experiments, and found that most decay fungi were inhibited. *Gliocladium viride*, a mycoparasite frequently isolated from chips, was tested on spruce chips in the field, and inhibited decay at temperatures less than 30° C., but failed at higher temperatures.

Conifer chips inoculated with an antibiotic-producing Cryptosporiopsis sp. and stored outdoors for 12-15 months yielded an improved quality of pulp although decay was not completely inhibited.[7] The results of trials using the antibiotic as a chemical preservative, and of a proposed field test, have not been published.

Bacteria were also tested as biological control agents in chip piles. Some bacteria isolated from hardwood chips were inhibitory to selected decay fungi in agar interactions, but the antagonism was only effective on wood when the bacteria were inoculated onto the wood several weeks before the decay fungi.[8] The results of a planned field trial were not published.

The possibility of controlling sapstain by using antagonistic organisms has also received some attention. The early work of Stilwell and his colleagues[9] demonstrated the antagonism of some microorganisms towards some sapstain fungi. Stranks[10] found that 0.25% and 0.50% solutions of the antibiotic hyalodendrin, applied to white pine blocks by dipping, were effective at preventing sapstain by Graphium sp., while cryptosporiopsin was ineffective. Seifert et al[11] screened a variety of microfungi for their abilities to prevent sapstain in precolonization experiments, and identified *Nectria cinnabarina, Gliocladium roseum,* Trichoderma spp. and Tympanis sp. as promising candidates. Russian workers[12] have demonstrated in vitro inhibition of sapstain fungi by unidentified bacteria, but have not demonstrated efficiency on wood. Bernier and colleagues[13] showed that an isolate of *Bacillus subtilus* prevented sapstain when wooden blocks dipped into a cell suspension were placed on agar plates inoculated with sap-staining fungi, but subsequent work at Forintek with the same culture showed that it did not inhibit sapstain when the wood was not placed on agar. The bacterium colonized wood very poorly and this prevented effective biological control. Benko[14] has recently screened many bacteria for antagonism towards sapstain fungi in agar interactions, and has selected some strains of Pseudomonas for further study.

Some innovative approaches towards biocontrol of sapstain have also been tried. Johnson[15] studied polyoxin, an antibiotic that inhibits the synthesis of chitin, a major component of fungal cell walls. The eight sapstain and mould species tested were sensitive to this compound but at concentrations too high to be economical on a commercial scale. Benko[16] demonstrated that crude culture extracts of some antibiotic producing mycorrhizal fungi prevented growth of several sap-staining fungi on blocks of pine.

The present invention employs a microorganism that has never before been considered as a possible biological control agent. The hyphomycete *Mariannaea elegans* (Corda) Samson is commonly reported from soil and litter in coniferous forests in the Northern hemisphere. The species is usually considered a soil fungus, but it is known to inhibit the growth of the mushroom *Pholiota nameko* (T. Ito) S. Ito & Imai at some temperatures. We have employed several different isolates of *M. elegans* that were found growing on different substrates in different locations in North America. All the tested isolates are effective biological control agents. The isolates which we have employed are identified as FTK 386A, 386B, 386C, 386D, 386E, 386which were collected independently from each other as follows 386A: isolated on 14/6/83 from hem-fir sapwood lumber (Vancouver B.C.) by W. C. Chang.

386B: isolated on 12/5/86 from bark beetle tunnels on fallen branch of *Pinus resinosa* (Ottawa, Ontario) by K. A. Seifert.

386C: isolated on 10/8/86 from *Pinus strobus* (Amherst, Massachusetts) by K. A. Seifert.

386D: isolated on 14/9/86 from *Abies balsamea,* (Val des bois, Quebec by K. A. Seifert.

386E: isolated on 17/9/86 from soil, using alkali extracted steam exploded aspenwood as the carbon source, (Ottawa, Ontario) by K. A. Seifert.

386F: isolated on 10/82 from pine litter (Devon, Alberta) by L. Sigler. Received from the University of Alberta Mould Herbarium.

386G: isolated on 05/67 from soil under pine (Petawawa, Ontario) by L. Sigler. Received from the University of Alberta Mould Herbarium.

The strains 386A, 386B, 386C, 386D and 386E are native to the Forintek Culture Collection, strains 386F and 386G were received from the University of Alberta Mould Herbarium. Cultures of the isolates referred to above are available upon request made to Forintek Culture Collection of Forintek Canada Corp., 800 Montreal Road, Ottawa, Ontario K1G 3Z5, Canada.

Our studies of the metabolites produced by *M. elegans* have demonstrated that it does not produce any known compounds toxic to mammals when grown on agar. Furthermore, the two isolates tested did not grow at 35° C. and therefore would be unable to grow at 37° C., the body temperature of humans.

The invention provides a method of controlling sapstain in wood and wood products comprising treating the wood or wood product with an inoculum of the fungus *Mariannaea elegans*.

The invention also provides a biological control agent for prevention of sapstain caused by fungi in lumber wherein said biological control agent is *Mariannaea elegans*.

The invention additionally provides a method of protecting freshly sawn timber during seasoning and prior to planing and chemical treatment of said timber, comprising treating said timber with an inoculum of the fungus *Mariannaea elegans*.

According to the invention, wood is treated with an inoculum of the biological control fungus *Mariannaea elegans*. The inoculum is of sufficient concentration and vigour to allow rapid colonization of the wood tissue by the inoculated biological control fungus. The actively growing and metabolizing biological control fungus does not itself damage or discolour the wood, but through antibiotic facilities or mycoparasitism protects against discoloration of the wood by undesirable organisms already present in the wood tissue, or that may be introduced to the wood tissues during handling of the lumber. Because the biological control fungus must subsist only on nonstructural wood carbohydrates, the control is of necessity short term, and can be expected to become ineffective upon depletion of the easily assimilable nutrients, perhaps up to one year after inoculation of the wood with the biological control agent.

The invention is intended for use primarily in situations where sapstain is prevalent, but for which chemical protection is impractical or impossible. Suggested applications include the protection of freshly sawn timber during seasoning, prior to planing and subsequent chemical treatment, protection of export lumber where chemical treatment, or specific chemical treatments, are forbidden by the importing countries, or treatment of wood chips during storage.

The examples below describe the effectiveness of *M. elegans* in preventing or inhibiting sapstain or sapstain fungi, and demonstrate that *M. elegans* does not itself damage wood.

EXAMPLE 1

Inoculum of the biological control agent is prepared by removing plugs of agar from stock cultures and growing them on agar in petri dishes. The growth medium employed is typically Difco, Potato Dextrose Agar (PDA) for *Mariannaea elegans* and 2% Difco malt extract with 2% agar (2% MA) for the sapstaining fungi.

Stock cultures are maintained at 4° C on agar media containing 2% Difco malt extract as a nutrient source. All other incubations described in this example are at 27° C, 75% relative humidity, in the dark.

The fungi used as biological control agents in this example are selected from the following strains maintained in the Forintek culture collection of wood-inhabiting fungi: *Mariannaea elegans* 386A, 386B, 386C, 386D, 386E, 386F or 386G. The sapstaining fungi employed are: *Ophiostoma piceae* 387I, *O. piliferum* (Fr.) H. & P. Sydow 55F, 55H and Ophiostoma sp. C28.

After 1–3 weeks, a plug from the colony of the biological control agent is placed on one side of 2% MA in a 9 cm petri dish, and a plug from the colony of the sapstaining fungus is placed on the opposite side of the petri dish, such that the two fungi will grow together near the centre of the plate. Each possible combination of biological control agent and sapstaining fungus is set up. The plates are observed periodically An identical set of interactions is set up using PDA.

On 2% MA, the biological control agent inhibits the growth of the sapstaining fungus when the two colonies touch in most cases, except for the isolate 386D, which does not obviously impede growth. On PDA and less often on 2% MA, a few isolates of *M. elegans* inhibit some sapstaining fungi before contact is made, indicating that antifungal metabolites are produced. The complete results are presented in Table 1.

EXAMPLE 2

Inoculum of the biological control agent is prepared as in example 1, using 2% MA. Stock culture maintenance and incubation conditions are as in example 1.

The fungi used as biological control agents in this example are selected from the following strains: *Mariannaea elegans* 386A, 386B, 386C and 386D.

After 1–3 weeks, the agar containing the culture of the biological control agent is transferred to a sterile Waring blender and homogenized in 75–150 mL sterile water for 30 seconds.

The pieces of wood used for this example are jack pine sapwood, 63 mm long, and 19 mm × 19 mm in cross section, sterilized by gamma irradiation. Each sterilized wood block is plac on a sterilized microscope slide on the solid surface of 10 mL of 1.5% tap water agar in an 8 ounce universal jar. Each jar is fitted with a special culture lid with a microbiological filter with a 0.2 μm pore size fitted over a 5 mm hole in the lid.

Sufficient homogenized culture is transferred to the top of each block using a sterilized pipette, such that enough liquid to cover most of the upper surface is present (for example, 0.3 mL). The wood thus inoculated is then incubated to allow proliferation of the biological control fungus in the wood.

After two weeks, the blocks are inoculated with sapstaining fungi. The sapstaining fungus inocula are prepared in an identical manner to the methods used for the biological control inocula. Three different sapstaining fungi are used: *Ophiostoma piliferum* 55F, Ophiostoma sp. C28 and *Ophiostoma piceae* 387C. One sapstaining fungus is inoculated onto each block and each biological control agent is tested against each of the four sapstaining fungi.

The wood blocks thus inoculated are incubated for a further four weeks.

After this time, the wood blocks are seen to be unstained by the sapstaining fungi. Control blocks inoculated at the same time are darkly stained by the sapstaining fungi. Analysis of the blocks with a quantitative assay for sapstaining fungi, the enzyme linked immunosorbent assay (ELISA), demonstrates that the amount of sapstaining fungi has been reduced by 60–99 % by the biological control agent, as detailed in Table 2.

In this example, strains 386B and 386C were most efficient at preventing growth of the sapstaining fungi, with growth reduced by 97% or more for all sapstaining fungi tested.

EXAMPLE 3

Inocula of the biological control fungi are prepared by transferring plugs of stock cultures onto PDA in 6 cm petri dishes. Stock culture maintenance and incubation conditions are as in example 1.

The biological control agents are selected from the following strains: *Mariannaea elegans* 386A, 386B, 386C, 386D, 386E.

The wood blocks used in this example are jack pine sapwood 3 cm long and 1 cm × 0.5 cm in cross section. These are sterilized by gamma irradiation and placed in glass petri dishes, eight blocks per dish, upon W-shaped glass bars fashioned from 3 mm glass tubing, that rest upon 2 sheets of filter paper in which 5 mL sterile distilled water has been absorbed.

After 1–3 weeks, a spore suspension is prepared from the agar cultures of 386B, 386C, 3B6D and 386E by pouring 5 mL of sterile distilled water into each petri dish. The spores are dislodged from the culture medium by using a sterile wire instrument, or by repeated washing with a narrow aperture syringe. The resulting spore suspension is then removed from the dish using a sterile syringe. For culture 386A, the agar colony is transferred into a sterile Waring blender then homogenized for 30 seconds in 75 mL sterile distilled water.

The inoculum is squirted onto the surface of each block in the petri dish such that the entire length of the block, though not necessarily the entire width, receives some liquid.

The blocks are then incubated for 1 week.

Staining fungus inocula are grown in 6 cm petri dishes on appropriate agar media for 1–2 weeks. Spore suspensions are prepared in the same way as described for the biological control strains above. The sapstaining fungi employed are: *Ophiostoma piceae* 387I, *O. piliferum* (Fr.) H. & P. Sydow 55F, 55H and Ophiostoma sp. C28.

The sapstaining fungus spore suspensions are then inoculated onto the surface of the wood blocks in a manner identical to that used for the biological control fungi.

The wood blocks are incubated a further four weeks.

The surface and interior of the wood blocks thus treated are free from discolorations caused by the sapstaining fungi, while control blocks inoculated at the same time with only sapstaining fungi become darkly discoloured after only 1–2 weeks. When the blocks are analyzed by ELISA, it is demonstrated that the amount of sapstaining fungi present in the blocks treated with the biological control agent is reduced by 85-100%, as detailed in Table 3.

In this example, all 5 strains of *Mariannaea elegans* reduced sapstain, but isolates 386C, 386D, and 386E reduced the amount of sapstain by 95% or more for all sapstaining fungi tested.

EXAMPLE 4

In this example, identical methods are used to those in Example 3, but the results are analyzed visually rather than with the ELISA. The biological control agents used are *Mariannaea elegans* 386F or 386G. The sapstaining fungi used are *Cephaloascus fragrans* 307I, *Ophiostoma piliferum* 55H, *Black Yeast* 86-10-1-1-1, and a mixture of eleven sapstaining fungi (the three fungi listed immediately above and *Aureobasidium pullulans* 132Q, *Leptodontidium elatius* 268A, *Cladosporium cladosporioides* 273D, *Ophiostoma populinum* 671A, *Ophiostoma perfectum* 703A, *Phialophora botulispora* 07A, *Leptographium* sp. 2A2 and *Phoma* sp. 86-8-3-2-1).

After the four week incubation period, the wood blocks have no visible signs of sapstain discolouration.

EXAMPLE 5

In this example, the same biological control agents and sapstaining fungi are used as in example 3. The method used is identical, except that the sapstaining fungi are inoculated onto the wood blocks first. One week later, the biological control agents are inoculated onto the blocks.

Significant sapstain occurs on the blocks in the one week before the biological control agent is added. When the blocks are analyzed with the ELISA at the end of the 4 week incubation, it is revealed that the amount of sapstain is reduced in some blocks relative to the controls by 9-75%. However, in some blocks, sapstain is not reduced and in others, the amount of sapstaining fungi present in the blocks is actually higher than in the control blocks not treated with biological control agents. These results are summarized in Table 4.

In this example, the isolates of Mariannaea elegans that reduced the amount of sapstain the most were 386B and 386E.

EXAMPLE 6

In this example, the ability of some isolates of *Mariannaea elegans* to cause weight loss in jack pine blocks is tested. The standard ASTM soil block test (D 1413-76) is used. In this method, 200 g of a 3:1 soil:sand mixture are placed in a 500 mL glass jar with 60 mL distilled water. A feeder strip made of red pine sapwood, 41×29×3.0 mm, is placed on the surface of the soil. The jars are sterilized for one hour, cooled, then resterilized for a second hour. The lids are then replaced with 7- sterile culture lids with a microbiological filter with a 0.2 $\mu\mu$m pore size fitted over a 5 mm hole in each lid. The soil is inoculated with an agar plug from a growing colony of *Mariannaea elegans* 386A or 386E, and incubated for 3 weeks. Then, two sterilized 19 mm cubes of jack pine sapwood of known dry weight are added to each jar. After 12 weeks incubation, the blocks are dried and reweighed.

The weight loss caused by *Mariannaea elegans* 386A was 0.2%, and that caused by 387E 1.3 %. A typical decay fungus, *Poria carbonica* 120AM, incubated under the same conditions, caused a weight loss of 33%.

Clearly, the tested strains of *Mariannaea elegans* cause little significant weight loss in wood.

EXAMPLE 7

In this example, the ability of some isolates of *Mariannaea elegans* to produce soft rot cavities in white birch is examined. Radial sections 20 $\mu$m thick are cut from wood blocks, 3×1×0.5 cm, using a sliding block microtome. After sterilization, the sections are placed in a two compartment 9 cm petri dish so that they form a bridge between 2% water agar on one side, and minimal agar on the other side. The minimal agar is composed of $NH_4NO_3$ 6.0 g, $K_2HPO_4$ 4.0 g, $KH_2PO_4$ 5.0 g, $MgSO_4.5H_2O$ 4 g, thiamine.HCl 0.02 g and agar 15 g, in 1000 mL distilled water. An agar plug from a growing colony of *Mariannaea elegans* 386A or 386E is placed onto the end of the wood embedded in the minimal agar, and the plates are incubated for four weeks.

Examination of the wood sections under the microscope using polarized light demonstrates that *Mariannaea elegans* 386A and 386E do not produce soft rot cavities on white birch. The known soft rot fungus *Chaetomium globosum* 172B produces abundant soft rot cavities under the same conditions. Therefore, *Mariannaea elegans* is unlikely to cause significant soft rot.

EXAMPLE 8

In this example, the ability of *Mariannaea elegans* 386E to cause strength loss in wood is determined. Small wood beams are incubated in a modified soil block test and the impact bending strength is measured using the ISOD machine, as detailed below.

The ISOD impact bending machine measures the force required to break a span of wood. A weight attached to a pendulum is released using a foot pedal, which pulls a chain attached to a vertical metal bar. The bar then is pulled into the sample (=impact), and the wood is broken. The force required to break the sample is determined by converting the value recorded by the pendulum of the machine (in degrees and minutes) to inch-pounds. The ISOD machine was modified for the smaller wood beams by reducing the weight on the pendulum and modifying the sample holder.

The soil block test was modified from ASTM standard D-1413 to allow for the different block sized. Rather than using glass jars, 1L Nalgene polypropylene jars are used. Each jar contains 400 g of a 3:1 soil:sand mixture and 120 mL of distilled water. Three red pine feeder strips, 4.5×2.5×0.5 cm, are placed side by side on the surface of the soil. The jars are autoclaved for one hour, cooled overnight, then autoclaved again the next day for one hour. The jars are cooled in a biological safety hood, and the lids replaced with culture lids. The culture lids are modified lids with a central hole, 5.16 of an inch in diameter, covered on the inner surface with a Gelman filter to allow air exchange.

The wood beams, 9.0×0.75×0.75 cm, are prepared from green pi *Pinus banksiana* sapwood. The beams are sorted into sets with more or less the same number of growth rings. Only beams with the grain more or less parallel to the long axis are selected. The beams are sterilized by gamma radiation and frozen until use.

The inoculum for *Mariannaea elegans* 386E is a spore suspension in water made from a 1-2 week old PDA culture. The spore suspension is inoculated onto the wooden beams, and the beams are preincubated for 1 week in a 1L Nalgene polypropylene jar. At the bottom of the jar is filter paper moistened with distilled water, then alternating layers of glass rods and wood beams. All beams used in the experiment are from a matched set.

After the preincubation period, five test beams are aseptically added to each soil jar. For controls, uninoculated test beams are aseptically added to jars. Five jars are set up for each treatment, for a total of 25 beams per treatment. All incubations are at 27° C.

After four weeks incubation, the beams are removed from the jars and placed on screen racks. The samples are then placed at a constant temperature and humidity and allowed to aquilibrate for 7 days. The force required to break each beam is then measured being the ISOD impact bending machine. The values are converted using the equation:

Toughness $(inch-pounds) = pendulum\ weight \times (cosA_2 - cosA_1)$ where $A_1$ is the initial angle, and $A_2$ is the angel of the pendulum at failure.

The readings given by the machine when no specimen was present are converted using the same equation, and this value is subtracted from the converted test values to give a corrected value.

Wood specimens colonized with *M. elegans* 386E require 12.87±0.32 inch-pounds to break. The control blocks, with no added fungus, require 12.74±0.44 inch-pounds to break. This demonstrates that *M. elegans* 386E does not cause strength loss in jack pine under the conditions employed.

TABLE 1-continued

Results of agar interactions between different isolates of *Mariannaea elegans* and selected sapstaining fungi on 2% malt agar and on Potato Dextrose Agar.

| M. elegans isolate | Sapstaining Fungus | | | | | | | |
|---|---|---|---|---|---|---|---|---|
| | 55F | | 55H | | 387I | | C28 | |
| | 2% MA | PDA | 2% MA | PDA | 2% MA | PDA | 2% MA | PDA |
| 386G | — | — | — | — | Anc | — | Anc | — |

Abbreviations used:
Ac = antagonism at contact between two colonies
Anc = Antagonism before contact between colonies
NA = No antagonism evident between colonies

TABLE 2

Biomass of sapstaining fungi detected in wood blocks precolonized with *Mariannaea elegans* and subsequently inoculated with sapstaining fungi as determined with an ELISA. Percentage values in brackets indicate colonization of the precolonized wood by the sapstaining fungi, relative to the controls.

| Precolonizing strain | Amount of sapstaining fungus (μg/mg dry wood) | | | | | |
|---|---|---|---|---|---|---|
| | C28 | | 55F | | 387C | |
| control | 20.8 | (100%) | 9.8 | (100%) | 7.6 | (100%) |
| 386A | 0.18 | (<1%) | 0.48 | (1.8%) | 3.2 | (40%) |
| 386B | 0.13 | (<1%) | 0 | (0%) | 0.2 | (2.5%) |
| 386C | 0.3 | (1.5%) | 0.16 | (2%) | 0.23 | (3%) |
| 386D | 0.28 | (1.3%) | 0.78 | (9.5%) | 0.1 | (1.3%) |

TABLE 3

Biomass of Ophiostoma spp. detected by ELISA in wood blocks precolonize *Mariannaea elegans* and subsequently inoculated with Ophiostoma spp.

| M. elegans strain | Biomass of Ophiostoma spp in μg/mg dry wood | | | | | | | |
|---|---|---|---|---|---|---|---|---|
| | C28 | | 55F | | 55H | | 387I | |
| none | 6.64 | (100%) | 7.54 | (100%) | 6.78 | (100%) | 2.11 | (100%) |
| 386A | 0.063 | (1.01%) | 0.315 | (4.05%) | 0.724 | (11.6%) | 0.322 | (15.7%) |
| 386B | 0.031 | (0.5%) | 0.78 | (0.77%) | 0.152 | (14.35%) | 0.134 | (7.25%) |
| 386C | 0.029 | (0.47%) | 0.023 | (0.27%) | 0.179 | (2.6%) | 0.082 | (3.85%) |
| 386D | 0.011 | (0.17%) | 0.136 | (3.96%) | 0.066 | (0.95%) | 0.046 | (2.4%) |
| 386E | 0.031 | (0.45%) | 0.075 | (0.55%) | 0.148 | (2.1%) | 0.076 | (3.7%) |

TABLE 4

Biomass of Ophiostoma spp. detected using ELISA in wood blocks precolonized with Ophiostoma spp. and subsequently inoculated with *Mariannaea elegans*.

| M. elegans strain | Biomass of Ophiostoma spp. in μg/mg dry wood | | | | | | | |
|---|---|---|---|---|---|---|---|---|
| | C28 | | 55F | | 55H | | 387I | |
| none | 7.65 | (100%) | 7.68 | (100%) | 10.18 | (100%) | 3.87 | (100%) |
| 386A | 5.52 | (74%) | 6.70 | (91.5%) | 9.54 | (121%) | 5.68 | (148%) |
| 386B | 3.66 | (51%) | 7.69 | (97%) | 2.41 | (24%) | 1.53 | (38%) |
| 386C | 4.74 | (60.5%) | 8.56 | (84%) | 4.7 | (47%) | 4.72 | (121%) |
| 386D | 1.33 | (20.5%) | 7.60 | (111%) | 5.64 | (63.5%) | 2.65 | (67.5%) |
| 386E | 5.31 | (74%) | 4.04 | (39.5%) | 6.52 | (73%) | 3.03 | (76.5%) |

TABLE 1

Results of agar interactions between different isolates of *Mariannaea elegans* and selected sapstaining fungi on 2% malt agar and on Potato Dextrose Agar.

| M. elegans isolate | Sapstaining Fungus | | | | | | | |
|---|---|---|---|---|---|---|---|---|
| | 55F | | 55H | | 387I | | C28 | |
| | 2% MA | PDA | 2% MA | PDA | 2% MA | PDA | 2% MA | PDA |
| 386A | Ac | Ac | Ac | Ac | Ac | Anc | Ac | Ac |
| 386B | Ac | Ac | NA | Ac | Ac | Anc | Ac | Anc |
| 386C | NA | Ac | Ac | Ac | Ac | Ac | Ac | Ac |
| 386D | NA | NA | NA | NA | NA | Ac | NA | Ac |
| 386E | Ac | Ac | Ac | Ac | Ac | Ac | Ac | Anc |
| 386F | Ac | — | Anc | — | Anc | — | Anc | — |

REFERENCES

1. Unligil, H. H. 1978. Decay resistance of wood treated with fungal antibiotics, cryptosporiopsin, hyalodendrin, and scytalidin. Wood. Sci. 11: 30–32.
2. Shields, J. K. 1966. Wood Pathology. Rept. For. Prod. Res. Branch, Dept. For. Can., April 1964–March 1965: 48–52.
3. Shields, J. K. 1968. Role of Trichoderma viride in reducing storage decay of birch logs. Bimonthly Res. Notes Dept. For. Can. 24: 9–10; Hulme, M. A. and J. K. Shields. 1972. Effect of primary fungal infection upon secondary colonization of birch bolts. Mat. und Org. 7: 177–188.

4. Stilwell, M. A. 1966. A growth inhibitor produced by *Cryptosporiopsis* sp., an imperfect fungus isolated from yellow birch, *Betula alleghaniensis* Britt. Can. J. Bot. 44: 249–267.

Strunz, G. M., A. S. Court, J. Komlossy and M. A. Stilwell. 1969. Structure of cryptosporiopsin: a new antibiotic substance produced by a species of Cryptosporiopsis. Can. J. Chem. 47: 2087–2094.

6. Bergman, 0. and T. Nilsson. 1979. Outdoor chip storage—methods of reducing deterioration during OCS. pp. 245–271. In: Chip Quality Monograph. Edited by J. V. Hatton. Pulp and Paper Tech. Ser. no. 5.

7. , M. A. and G. M. Strunz. 1967. Antibiotic produced Stilwell by a fungus. Rept. CFS For. Res. Lab., Fredericton, N. B.

8. Lapetite, D. 1970. Etude sur bois de 'action antagoniste des bactéries vis-à-vis des champignons lignivores. Mat. und Ord. 5: 229–237.

Supra 7; Stilwell, M A., R. E. Wall and G. M. Strunz.

9. Supra 4; 1973. Production, isolation and antifungal activity of scytalidin, a metabolites of Scytalidium sp. Can. J. Microbiol. 19: 597–602; Strunz, G. M., M. Kakushima and M. A. Stilwell. 1973. Scytalidin: a new fungitoxic metabolite produced by a Scytalidium species. J. Chem. Soc. Perkin Trans. 1: 2280–2283.

10. Stranks, D. 1976. Scytalidin, hyalodendrin, cryptosporiopsis—Antibiotics for prevention of blue stain in white pine sapwood. Wood. Sci. 9: 110–112.

11. Seifert, K. A., C. Breuil, M. Best, L. Rossignol and J. N. Saddler. Screening of microorganisms with the potential for biological control of sapstain on unseasoned lumber. Mat. und Org.: 23 BD Heft 2.

REFERENCES (cont'd)

12. Vasiliev, O.A. 1968. (On the question of using the antagonism of fungi and bacteria for the protection of wood). Mach. Trudy Leningr. Lesotekh Akad. 110: 28–33 (in Russian).

13. Bernier, R. Jr., M. Desrocher and L. Jurasek. 1986. Antagonistic effect between Bacillus subtilus and wood staining fungi. J. Inst. Wood. Sci. 10, 214–216.

14. Benko, R. 1988. Bacteria as possible organisms for biological control of blue stain. Int. Res. Group on Wood Preserv., Document No. IRG/WP/1339.

15. Johnson, B. R. 1986. Sensitivity of some wood stain and mold fungi to an inhibitor of chitin synthesis. For. Prod. J. 36(3): 54–56.

16. Benko, R. 1987. Antagonistic effect of some mycorrhizal fungi as biological control of sapstain. Int. Res. Group on Wood Preserv., Document No. IRG/WP/1314.

WHAT WE CLAIM AS OUR INVENTION IS:

1. A method of controlling sapstain in wood and wood products comprising treating the wood or wood product with an inoculum of the fungus *Mariannaea elegans*.

2. The method according to claim 1 wherein the said fungus is selected from the group consisting of or more the following strains of *Mariannaea elegans* FTK 386A, 386B, 386C, 386D, 386E, 386F and 386G.

3. The method according to claim 1 wherein the wood or wood product is softwood lumber.

4. The method according to claim 1, wherein said inoculum includes spores of said fungus.

5. The method according to claim 1, wherein said inoculum includes homogenized mycelium of *Mariannaea elegans*.

6. A method according to claim 1 wherein said wood or wood products are wood chips.

7. The method according to claim 3 wherein said lumber is selected from the group consisting of birch, pine, Douglas fir, spruce and hemlock.

8. The method according to claim 1 wherein said wood or wood products are selected from the group consisting of hem-fir, spruce-pine-fir, white pine, jack pine and white birch.

9. The method according to claim 3 wherein said lumber has been cut, but has not been subjected to seasoning or chemical treatment.

10. A method of protecting freshly sawn timber during seasoning and prior to planing and chemical treatment of said timber, comprising treating said timber with an inoculum of the fungus *Mariannaea elegans*.

11. A method according to claim 10 wherein said fungus is selected from the group consisting of or more the following strains of *Mariannaea elegans*: FTK 386A, 386B, 386C, 386D, 386E, 386F and 386G.

12. The method of claim 1, wherein the treatment is used to prevent or inhibit sapstaining as a result of subsequent colonization by sapstaining fungi.

13. The method of claim 12, wherein the level of sapstaining fungus four weeks after colonization is reduced by at least about 85% relative to unprotected wood.

14. The method of claim 1, wherein said treatment does not cause substantial weight loss, strength loss or soft rot in the wood or wood product, or itself discolor the wood or wood product.

15. A treated wood or wood product obtained by treating an untreated wood or wood product selected from the group consisting of lumber or a wood product made from lumber, that, at the time of treatment, does not already bear a sapstain-inhibitory strain of *Mariannea elegans*, with a biological control agent comprising a suspension of spores of one or more sapstain-inhibitory strains of *Mariannea elegans* in a carrier suitable for the treatment of the untreated wood or wood product, said treated wood or wood product retaining said agent in viable form and being essentially free of sapstain as a result of the activity of said agent, said treated wood or wood product also being substantially free of discoloration caused by said agent or of strength loss, dry rot or weight loss caused by said agent.

16. The treated wood or wood product of claim 15, said wood or wood product being a softwood.

* * * * *